United States Patent
Li

(10) Patent No.: US 11,586,742 B2
(45) Date of Patent: Feb. 21, 2023

(54) DATA PROCESSING METHOD, DATA PROCESSING DEVICE, AND COMPUTER READABLE STORAGE MEDIUM

(71) Applicant: BOE TECHNOLOGY GROUP CO., LTD., Beijing (CN)

(72) Inventor: Zhenglong Li, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 619 days.

(21) Appl. No.: 16/332,314

(22) PCT Filed: Apr. 13, 2018

(86) PCT No.: PCT/CN2018/082998
§ 371 (c)(1),
(2) Date: Mar. 11, 2019

(87) PCT Pub. No.: WO2018/214669
PCT Pub. Date: Nov. 29, 2018

(65) Prior Publication Data
US 2019/0220606 A1 Jul. 18, 2019

(30) Foreign Application Priority Data
May 22, 2017 (CN) .......................... 201710365945.7

(51) Int. Cl.
*G06F 21/60* (2013.01)
*H04L 9/08* (2006.01)
(Continued)

(52) U.S. Cl.
CPC ........ *G06F 21/602* (2013.01); *G06F 21/6245* (2013.01); *G16H 30/20* (2018.01);
(Continued)

(58) Field of Classification Search
CPC . G06F 21/602; G06F 21/6245; H04L 9/0866; H04L 9/0861; H04L 9/0625;
(Continued)

(56) References Cited

U.S. PATENT DOCUMENTS 9,378,380 B1 6/2016 Reid et al.
2002/0156650 A1* 10/2002 Klein .................... G16H 40/67
705/2

(Continued)

FOREIGN PATENT DOCUMENTS

| CN | 101729256 A | 6/2010 |
| CN | 103312738 A | 9/2013 |
| CN | 105989297 A | 10/2016 |
| CN | 107194267 A | 9/2017 |

OTHER PUBLICATIONS

Search Report dated Jul. 2, 2018, which issued in International Patent Application No. PCT/CN2018/082998.

*Primary Examiner* — Noura Zoubair
*Assistant Examiner* — Aubrey H Wyszynski
(74) *Attorney, Agent, or Firm* — McDermott Will & Emery LLP

(57) ABSTRACT

The present disclosure provides a data processing method, a data processing device, and a computer readable storage medium. The data processing method includes: determining an encryption key according to first data; encrypting second data with the encryption key; and storing the first data in association with the encrypted second data.

12 Claims, 5 Drawing Sheets

(51) Int. Cl.
  *G16H 30/20* (2018.01)
  *H04L 9/06* (2006.01)
  *G06F 21/62* (2013.01)
  *H04L 9/00* (2022.01)

(52) U.S. Cl.
  CPC .......... *H04L 9/0625* (2013.01); *H04L 9/0643* (2013.01); *H04L 9/0861* (2013.01); *H04L 9/0866* (2013.01); *H04L 9/50* (2022.05); *H04L 2209/88* (2013.01)

(58) Field of Classification Search
  CPC ............... H04L 9/0643; H04L 2209/38; H04L 2209/88; G16H 30/20; G16H 10/60; G16H 30/40; G16H 40/20
  USPC .......................................................... 713/189
  See application file for complete search history.

(56) References Cited

U.S. PATENT DOCUMENTS

| | | | |
|---|---|---|---|
| 2003/0132285 A1* | 7/2003 | Blancas | G06Q 20/341 235/380 |
| 2003/0223614 A1* | 12/2003 | Robins | H04N 1/32144 382/100 |
| 2005/0251006 A1* | 11/2005 | Dellis | G16H 30/20 600/407 |
| 2006/0009692 A1* | 1/2006 | Fukuda | G16H 30/40 600/407 |
| 2011/0185177 A1* | 7/2011 | Spalka | H04L 9/3247 713/171 |
| 2011/0302414 A1* | 12/2011 | Logan | G16H 80/00 713/168 |
| 2015/0026461 A1* | 1/2015 | Devi | H04L 9/0894 713/165 |
| 2017/0277831 A1* | 9/2017 | Ruff | A61B 6/485 |
| 2019/0220606 A1 | 7/2019 | Li | |

* cited by examiner

DATA PROCESSING METHOD, DATA PROCESSING DEVICE, AND COMPUTER READABLE STORAGE MEDIUM

CROSS REFERENCE TO RELATED APPLICATION(S)

This application is a Section 371 National Stage Application of International Application No. PCT/CN2018/082998, filed on Apr. 13, 2018, entitled "DATA PROCESSING METHOD, DATA PROCESSING DEVICE AND COMPUTER READABLE STORAGE MEDIUM", which claims priority to Chinese Application No. 201710365945.7 filed on May 22, 2017, which is incorporated herein by reference in its entirety.

TECHNICAL FIELD

The present disclosure relates to a data processing method, a data processing device, and a corresponding computer readable storage medium.

BACKGROUND

As an important management and constitution part of a modern hospital, a Hospital Information System (HIS) is a software platform that mainly focuses on management needs of the hospital. In many implementations, the HIS is a comprehensive integrated information system designed to manage all aspects of hospital operations, such as medical, human, financial, legal issues, and corresponding service processing.

SUMMARY

According to a first aspect of the present disclosure, a data processing method is provided. The data processing method includes: determining an encryption key according to first data; encrypting second data with the encryption key; and storing the first data in association with the encrypted second data.

In some embodiments, the determining the encryption key according to the first data includes: determining a digital digest of the first data as the encryption key.

In some embodiments, the encryption key is a symmetric encryption key. In other words, the determining the encryption key according to the first data includes: generating a symmetric encryption key as the encryption key using a symmetric encryption algorithm.

In some embodiments, the first data includes a medical image, and the second data includes additional information associated with the medical image.

In some embodiments, the additional information is a diagnostic report corresponding to the medical image.

In some embodiments, the digital digest is determined by a hash list or a Merkle tree.

In some embodiments, the encrypting the second data with the encryption key includes: encrypting the second data using a data encryption standard (DES) encryption algorithm.

According to a second aspect of the present disclosure, a data processing method is provided. The data processing method includes: acquiring first data and encrypted second data; determining a decryption key according to the first data; and decrypting the encrypted second data with the decryption key to obtain second data.

In some embodiments, the determining the decryption key according to the first data includes: determining a digital digest of the first data as the decryption key.

In some embodiments, the determining the decryption key according to the first data includes: generating a symmetric decryption key as the decryption key using a symmetric encryption algorithm.

In some embodiments, the first data includes a medical image, and the second data includes additional information associated with the medical image.

In some embodiments, the additional information is a diagnostic report corresponding to the medical image.

In some embodiments, the digital digest is determined by a hash list or a Merkle tree.

In some embodiments, the decrypting the encrypted second data with the decryption key includes: decrypting the encrypted second data using a data encryption standard (DES) decryption algorithm.

According to a third aspect of the present disclosure, a data processing device is provided. The data processing device includes: an encryption key determination circuit configured to determine an encryption key according to first data; an encryption circuit configured to encrypt second data with the encryption key; and a data storage circuit configured to store the first data in association with the encrypted second data.

According to a fourth aspect of the present disclosure, a data processing device is provided. The data processing device includes: a data acquisition circuit configured to acquire first data and encrypted second data; a decryption key determination circuit configured to determine a decryption key according to the first data; and a decryption circuit configured to decrypt the encrypted second data with the decryption key to obtain second data.

According to a fifth aspect of the present disclosure, a data processing device is provided. The data processing device includes: a processor; and a memory storing instructions that, when executed by the processor, cause the processor to determine an encryption key according to first data; encrypt second data with the encryption key; and store the first data in association with the encrypted second data.

According to a sixth aspect of the present disclosure, a data processing device is provided. The data processing device includes: a processor; and a memory storing instructions that, when executed by the processor, cause the processor to acquire first data and encrypted second data; determine a decryption key according to the first data; and decrypt the encrypted second data with the decryption key to obtain second data.

According to a seventh aspect of the present disclosure, a data processing system is provided, which includes the data processing device according to the third or the fifth aspect of the present disclosure and the data processing device according to the fourth or the sixth aspect of the present disclosure.

According to an eighth aspect of the present disclosure, a computer readable storage medium storing instructions is provided. The instructions, when executed by a processor, cause the processor to perform one or more steps of the method of any one of the embodiments of the present disclosure.

BRIEF DESCRIPTION OF THE DRAWINGS

The above and other objects, features and advantages of the present disclosure will become more apparent from the detailed description in conjunction with the drawings, in which.

DETAILED DESCRIPTION

Figure 1:
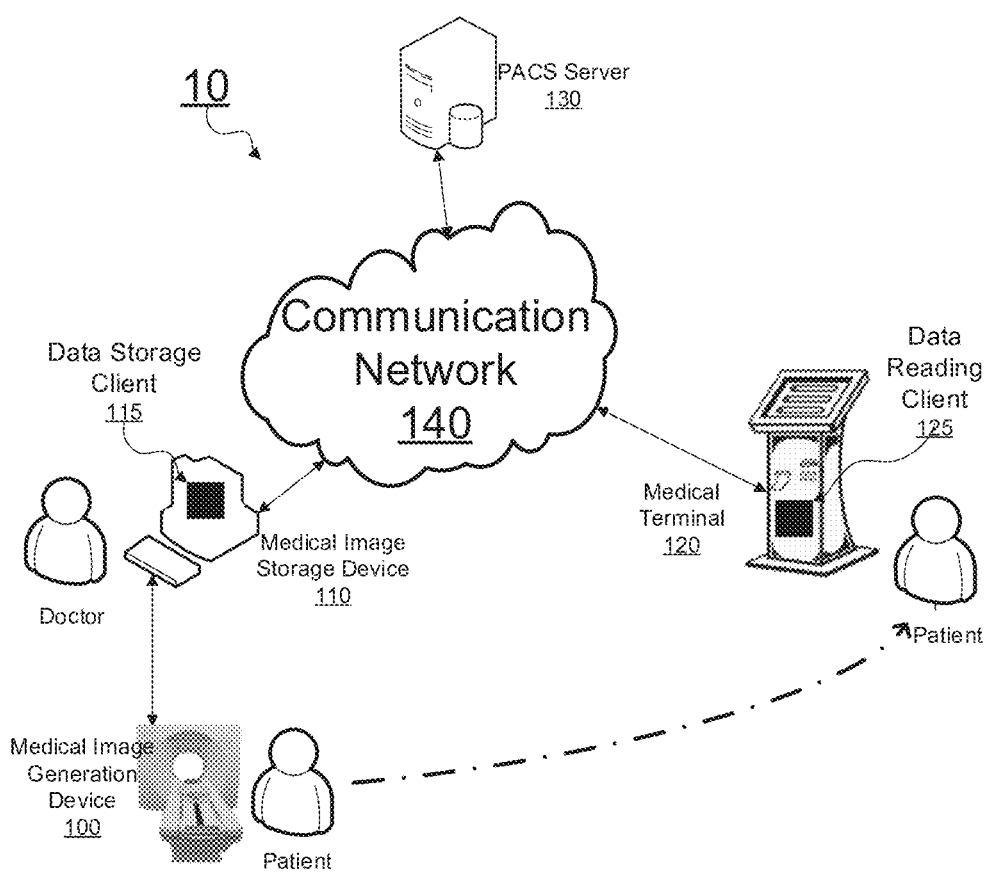
FIG. 1 is a schematic diagram showing an exemplary application scenario of a system for managing data storage in accordance with an embodiment of the present disclosure.

The embodiments of the present disclosure will be described in detail below with reference to the accompanying drawings, and the details and functions that are not necessary for the present disclosure are omitted in the description to avoid confusion of the understanding of the present disclosure. In the present specification, the following various embodiments for describing the principles of the present disclosure are merely illustrative, but should not be construed as limiting the scope of the present disclosure. The following description made with reference to the drawings may be used for facilitating to understand the exemplary embodiments of the present disclosure which are limited by the claims and the equivalents thereof. The following description includes numerous specific details to assist the understanding, but these details should be considered as merely exemplary. Accordingly, it will be appreciated by the skilled in the art that various changes and modifications may be made to the embodiments described herein without departing from the scope and spirit of the present disclosure. In addition, descriptions of well-known functions and constructions will be omitted for clarity and conciseness. Further, the same reference numerals are used throughout the drawings for the same or similar functions and operations. In addition, the parts are not necessarily drawn to scale in the drawings. In other words, the relative sizes, lengths, and the like of the respective portions in the drawings do not necessarily correspond to their actual ratios. In addition, different technical features in different embodiments may be combined to form new embodiments that fall within the scope of the present disclosure.

In the present disclosure, the terms "comprising" and "including" and their derivatives are meant to be inclusive but not limiting; and the term "or" is inclusive and means and/or.

As known by the inventors, the HIS is usually composed of one or more software components with special extensions, and has a large number of different medical subsystems from many providers, for example, a Laboratory Information System (LIS). A Policy and Procedure Management System (PPMS), a Radiology Information System (RIS) or a Picture Archiving and Communication System (PACS), etc.

Among these subsystems, PACS is a subsystem mainly used to manage, store and retrieve medical image data. Different from general images, the medical image, such as an X-ray imaging image, a B-mode ultrasound image, a DR (Digital X-Ray) image, a CT (Computed Tomography) image, an MRI (Magnetic Resonance Imaging) image, and/or a PET (Positron Emission Tomography) image, is usually accompanied with an additional diagnostic report of a relevant doctor. In order to achieve a one-to-one correspondence between the medical image and the additional diagnostic report, the general methods include: (1) making a mark on the medical image, e.g., a stamp-like numerical number or a patient name on an X-ray film, and meanwhile the additional diagnostic report also has the number of the X-ray film; or (2) directly embedding the image into the diagnostic report, e.g., for the diagnostic report of the B-mode ultrasound, the B-mode ultrasound image is usually embedded into the data structure of the diagnostic report.

The inventors have realized that the above methods have more or less problems as described below, such as a data integrity issue, a completeness issue of image information saving, etc.

Among them, the data integrity refers to the fact that the image data and the diagnostic report usually have a one-to-one correspondence. However, the PACS system in the related art cannot guarantee a strict correspondence between the image data and the diagnostic report. That is, neither the hospital nor the patient can prevent such a case that either the image data or the diagnostic report is tampered or the content is changed.

The completeness of the image information saving refers to the fact that in addition to the pixel information for display, various metadata included in the medical image, such as the resolution of the image, the shooting time, and the like, are saved when the medical image is saved. However, when the PACS system in the related art embeds image data into the diagnostic report (for example, embedding the image into a rich text data structure similar to Word), the resolution of the image is usually lowered in order to control the file size of the rich text, which causes that the original image information cannot be saved to a maximal extension. In addition, for the medical image data, in addition to the pixel information for display, other types of metadata, such as the display specification (such as the resolution, etc.), the shooting time, the serial number of the used device, the characteristics of the used device, etc., cannot be saved when the manner of embedding the image is used. Furthermore, in the process of circulating and exchanging the medical image within the medical system, the use of the rich text structure similar to Word cannot guarantee the accuracy of the medical image information.

Accordingly, in order to at least partially solve or alleviate the above problems, a method and a device for storing data, a method and a device for reading data, and a corresponding computer readable storage medium are provided in accordance with the embodiments of the present disclosure.

Hereinafter, the present disclosure will be described in detail by taking the present disclosure being applied in the field of medical information as an example. However, the present disclosure is not limited thereto, and is also applicable to any other suitable data storage/reading field. For example, in any application that needs to store first data and second data in association with each other and needs to ensure their completeness and to ensure that they cannot be tampered, the technical solutions according to the embodiments of the present disclosure may be applied.

As described above, in order to at least partially solve or alleviate the foregoing problems, the embodiments of the present disclosure propose a scheme of ensuring the medical image integrity based on an encryption technology. This scheme may ensure the integrity of the patient's medical image and the corresponding information (e.g., a diagnostic advice from the radiological department). That is, it is ensured that neither the hospital nor the patient can tamper with or alter the original image or its related information (e.g., the diagnostic advice from the radiological department). At the same time, this scheme can be seamlessly integrated into the PACS system, enabling the data access to be transparent to the operator.

In the following embodiments, some of the technical terms are described as follows.

Digital Digest: The digital digest process is a process of turning a message of any length into a short message of a fixed-length. It is similar to a function in which its argument is a message, usually a hash function. The digital digest is "digesting" the plaintext that needs to be encrypted into a series of ciphertext with a fixed-length (e.g., 128-bit) using a unidirectional hash function. The series of ciphertext is also referred to as a digital fingerprint, and has a fixed length. The digests are usually different for different plaintexts; while for the same plaintext, the digests must be consistent. The digital digest is often used to ensure the completeness of the original data and ensure that the original data cannot be tampered, and may be used for e.g., a digital signature.

Hash Function/Hash Value: The hash function is any function that can be used to map data of any length to data of a fixed-length. The value returned by the hash function is called a hash value, a hash code, a digest, and so on. It is widely used in the computer software for fast data lookups. The hash function may speed up lookups for tables or databases by detecting duplicate records in large files. An example is finding similar fragments in a DNA sequence. In addition, the hash functions/hash value is also widely used in cryptography. The hash function allows one party to easily verify that some input data is mapped to a given hash value, but if the input data is unknown, it is not possible to reconstruct the input data by learning the corresponding hash value. This is very useful in ensuring the completeness of the transmitted data and that the transmitted data cannot be tampered. As an important example of the hash function, an MD5 algorithm that generates a 128-bit hash value may be used in the embodiment of the present disclosure (however, the present disclosure is not limited thereto, and other suitable hash functions, such as SHA1, loop redundancy check, checksum, etc., may be used). In general, the hash function can be considered to have such a characteristic that even if the input data changes little, e.g., by one or more bytes, the generated hash value may usually change significantly (for example, at least a half of bits of its bit value are inverted, etc.).

MD5 (Message Digest 5): The MD5 algorithm is a widely used hash algorithm that produces a 128-bit hash value. Although the MD5 was initially designed to be used as an encryption hash function, it may also be used as a checksum for verifying the completeness of the data. In the MD5 algorithm, the input message is divided into 512-bit data segments (i.e., 16 32-bit words), and if it cannot be divided exactly, it may be supplemented in such a way as follows, so that it is divisible by 512. First, a single bit "1" is added to the end of the input message; the message is then supplemented with bit(s) "0" till a difference of 64 bits from an integer multiple of 512 bits is reached; the difference of the 64 bits is filled with 64 bits which are the length of the original input message module $2^{64}$; then the 512-bit data segments are operated according to predetermined rules, including shifting, swapping, logical operations (exclusive OR, AND, OR, NO, etc.) to obtain the final 128-bit hash value.

Hash List: A hash list is a list consisting of hash values of data blocks in a file or a collection of files. The hash list may be used in many scenarios, such as fast table lookups (hash tables) and distributed databases (distributed hash tables). It may also be used to ensure the completeness of the data as described below. A hash list is a conceptual extension of a hash function. Specifically, it may divide a larger file into a plurality of data blocks, calculate a hash value for each data block, and save and transfer these hash values in a form of a list. Thus, the receiving party of the data may quickly and conveniently verify the received data, and quickly determine which part of the data may be problematic.

Merkle Tree: Similar to the hash list, the Merkle tree or the hash tree is also a tree-type data structure for hashing big data. In the Merkle tree, each non-leaf node is marked with a label or a value of its child node (in the case of the leaf node). The hash tree allows verifying the content of the large data structure efficiently and safely. In some sense, the hash tree is a promotion of the hash list and the hash chain. To prove that some leaf node is a part of a given hash tree, it is required to process the amount of data which is proportional to the logarithm of the number of nodes in the tree. This is much less computational, compared to the hash list that requires to process an amount of data which is proportional to the number of the nodes.

Symmetric Encryption: The symmetric encryption is an encryption algorithm in which both the plaintext encryption party and the ciphertext decryption party use the same key. The shared key is the same for both parties or may be given by a simple transformation. The shared key actually embodies the secret shared between two or more parties for maintaining the private information link. Common symmetric encryption algorithms include, but are not limited to, Data Encryption Standard (DES), Triple Data Encryption Standard (3DES), Advanced Encryption Standard (AES), CAST (which is entitled by abbreviations of the first letters of the inventors of this algorithm).

Asymmetric Encryption: The asymmetric encryption, also referred to as public/private key encryption, is an encryption algorithm that uses a pair of keys, in which the public key may be publicly distributed, while the private key is only kept by the owner. It implements two functions: (1) authentication, when the private key owner issues a message encrypted or signed with the private key, the public key may be used to verify whether the message was issued by the private key owner, i.e., the authenticity, the non-repudiation; and (2) encryption, when the public key owner issues a message encrypted with the public key, only the private key owner can decrypt and read the message, avoiding the intervention of a third party. Common asymmetric encryption algorithms include, but are not limited to, an elliptic curve encryption algorithm, RSA (which is entitled by abbreviations of the first letters of the inventors of this algorithm) algorithm, a Diffie-Hellman encryption algorithm, an ElGamal (which is entitled by abbreviations of the first letters of the inventors of this algorithm) encryption algorithms, and so on.

DES encryption algorithm: The DES encryption algorithm, also referred to as a data encryption standard algorithm, is a widely used symmetric encryption algorithm for encrypting electronic data. It is characterized by fast speed and is suitable for high-speed, real-time encryption of data. In addition, as an enhanced version, there is also a 3DES (Triple DES) encryption algorithm.

Hereinafter, an example application scenario according to an embodiment of the present disclosure will be described in detail in conjunction with FIG. 1.

FIG. 1 is a schematic diagram showing an exemplary application scenario of a system 10 for managing data storage in accordance with an embodiment of the present disclosure. As shown in FIG. 1, the system 10 may include a medical image generation device 100, a medical image storage device 110, a medical terminal 120, and a PACS server 130.

In order to store data on the medical image storage device 110, a data storage client 115 (hereinafter simply referred to as a client 115) according to an embodiment of the present disclosure may be installed on the medical image storage device 110. The client 115 may be installed by the software provider in the medical image storage device 110 in the form of software, or may be installed by the device manufacturer in the medical image storage device 110 in the form of hardware or firmware.

In some embodiments, the client 115 may be, for example, application software which is specifically for use in the embodiments of the present disclosure and downloaded from the network after the user purchases the medical image storage device 110. In some embodiments, the client 115 may be an application that is pre-installed in the medical image storage device 110 by, for example, the device manufacturer in firmware or hardware. In some embodiments, the client 115 may be a hardware module or the medical image storage device 110 itself, which is produced by the device manufacturer.

For convenience of description, the client 115 and the medical image storage device 110 are considered to be interchangeable terms in the following description, unless otherwise specified.

In order to read data on the medical terminal 120, a data reading client 125 (hereinafter simply referred to as a client 125) according to an embodiment of the present disclosure is installed on the medical terminal 120. The client 125 may be installed by the software provider in the medical terminal 120 in the form of software, or may be installed by the device manufacturer in the medical terminal 120 in the form of hardware or firmware. In some embodiments, the client 125 may be, for example, application software which is specifically for use in embodiments of the present disclosure and downloaded from the network after the user purchases the medical terminal 120. In some embodiments, the client 125 may be an application that is pre-installed in the medical terminal 120 by, for example, the device manufacturer in firmware or hardware. In some embodiments, the client 125 may be a hardware module or medical terminal 120 itself, which is produced by the device manufacturer.

For convenience of description, the client 125 and the medical terminal 120 are considered to be interchangeable terms in the following description, unless otherwise specified.

The system 10 according to an embodiment of the present disclosure is not limited to the above configuration. In some embodiments, the system 10 may include additional other nodes, or may not include some one or more of the aforementioned nodes, or a combination thereof. For example, the system 10 may not include the medical terminal 120. Instead, the system 10 may include another medical image storage device 110 capable of reading data of the medical terminal 120. That is, the medical image storage device 110 may be a device that is used for both data storage and data reading. For example, when a physician needs to read image data, which are stored by a radiologist in a medical image storage device 110 (e.g., a device connected to an X-ray apparatus) in a radiology department, on his own medical image storage device 110 (e.g., a device connected to a handheld B-ultrasound instrument), the functions of the medical terminal 120 or the data reading client 125 may be performed on the medical image storage device 110. In addition, the PACS server 130 can also be integrated with other nodes, such as the medical image storage device 110 and/or the medical terminal 120.

The medical image generation device 100 may be a medical image generation device 100 such as an X-ray imaging machine, a CT machine, an MRI machine, a handheld B-ultrasound instrument, and the medical image storage device 110 may be a medical computer (e.g., a desktop, notebook, terminal, or any special or general purpose computing device, etc.) connected with the medical image generation device 100 in a wired or wireless way. The doctor may obtain the medical image (e.g., an X-ray film, CT imaging, MRI imaging, B-ultrasound imaging, etc., which may be generally referred to as "first data" herein) of the patient from the medical image generation device 100 by, for example, operating the medical image storage device 110. When the doctor reviews the medical image, he may give a corresponding diagnosis report (e.g., generally referred to as "second data" herein) based on the patient's symptoms reflected in the medical image, transmit the diagnosis report in association with the medical image to the PACS server 130, and store the diagnosis report in association with the medical image in the PACS server 130.

The patient (or other person) who has finished his examination may obtain a corresponding examination report after a certain period of time by, for example, the medical terminal 120 installed in the hospital lobby. For example, the patient may request the examination report from the PACS server 130 by entering an identification (ID) number, a medical record number, a checklist two-dimensional (2D) code, etc. in the medical terminal 120. Upon receiving the request, the PACS server 130 may retrieve the corresponding medical image and the associated diagnosis report according to the ID number, the medical record number, the checklist 2D code, etc. included in the request, and feed it back to the patient via the medical terminal 120.

However, as previously mentioned, since there is a possibility that any one or both of the parties may tamper with the medical image and/or the examination report, the data storage approach in the foregoing example cannot guarantee the completeness of the medical image and/or the examination report and that the medical image and/or the examination report cannot be tampered. Therefore, there is a need for a method that can guarantee the completeness of the medical image and that the medical image cannot be tampered. This method may ensure the integrity of the patient's medical image and its related information (e.g., the radiology diagnostic advice), i.e., ensuring that any of the parties cannot tamper with or alter the original image or its related information (e.g., the radiology diagnostic advice). At the same time, this method may be seamlessly integrated into the PACS system, enabling the data access to be transparent to the operator.

Hereinafter, a message flow of achieving secure storage of data between various nodes in the exemplary scenario of FIG. 1 will be described in detail in conjunction with FIG. 2.

Figure 2:
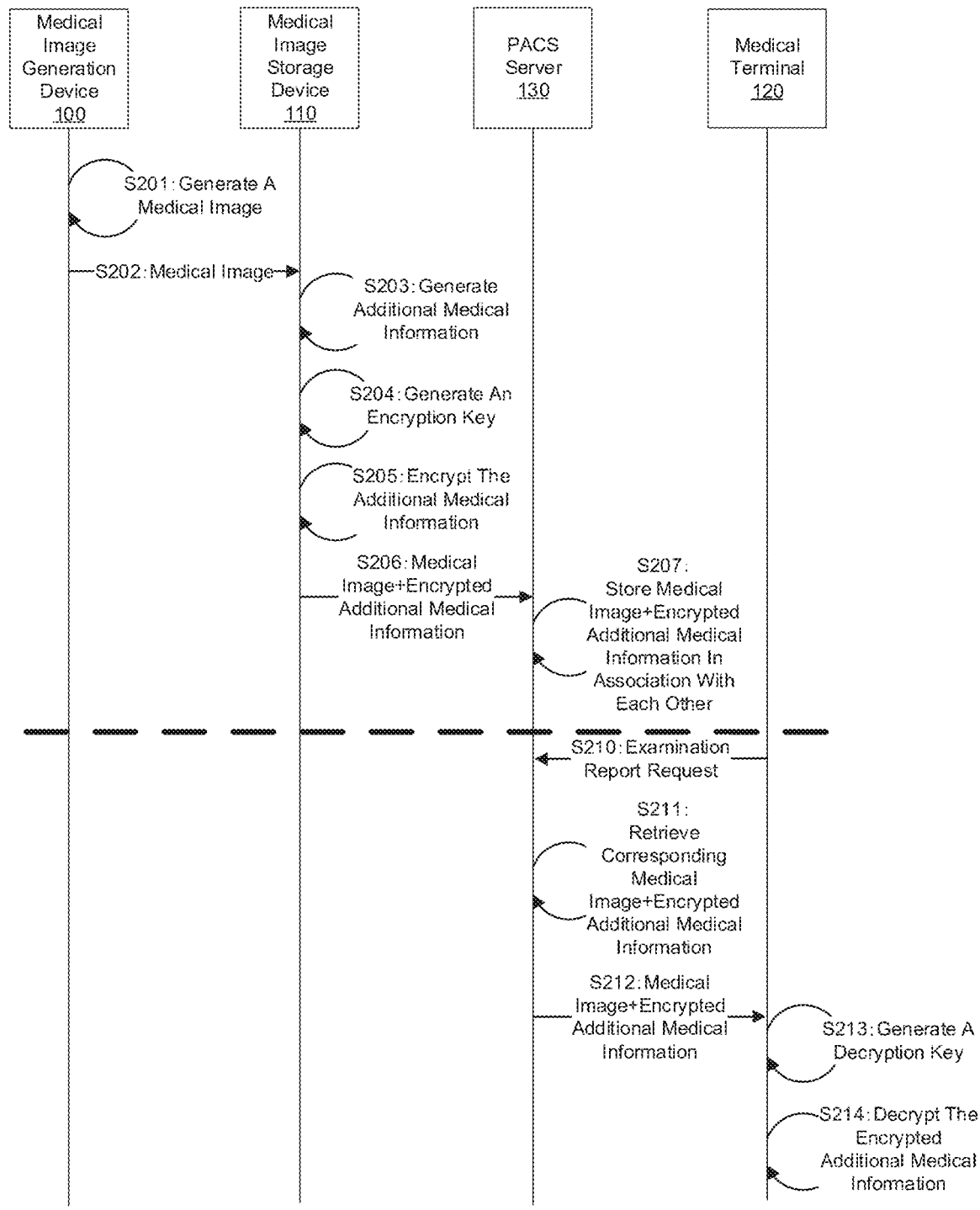
FIG. 2 is a diagram showing an exemplary message flow for managing data storage between various nodes as shown in FIG. 1 in accordance with an embodiment of the present disclosure.

FIG. 2 is a diagram showing an exemplary message flow for managing data storage between various nodes as shown in FIG. 1 in accordance with an embodiment of the present disclosure.

As shown in FIG. 2, the medical image generation device 100 generates a medical image in step S201, and transmits the medical image to the medical image storage device 110 in step S202. In view of the similarities with the foregoing process, it will not be described in detail herein.

In step S203, the medical image storage device 110 that has received the medical image may generate additional medical information based on the medical image. For example, when the medical image storage device 110 receives the medical image, it may display the medical image to the associated person (e.g., a doctor or any other relevant person), and receive the associated additional information input (e.g., diagnostic text input, diagnostic options check input, hospital card swiping input, etc.) to generate or determine the additional information.

In general, the additional information may be other types of metadata included in the medical image itself other than the pixel information used for display, such as the display specification (such as the resolution, etc.), the shooting time, the serial number of the used device, etc., and/or the diagnosis and treatment information and medical record information (not included in the medical image) formed by medical service related personnel, which may include, but is not limited to, e.g. at least one of: the patient's name, ID number, or other identities (e.g., patient number of hospital), medical history, age, gender, any physiological/psychological indicators, diagnostic advice, medication recommendations, or any other data.

In some embodiments, the additional information is a diagnostic report corresponding to the medical image. For example, the medical image is an X-ray film, and the diagnostic report is a radiology diagnostic advice corresponding to the X-ray film.

In step S204, an encryption key for encrypting the additional medical information (or the second data) may be determined according to the medical image (or the first data).

In some embodiments, the encryption key may be a digital digest of the medical image.

In some embodiments, the digital digest may be, for example, an MD5 value or other hash value of medical image data.

In step S205, the additional medical information may be encrypted using the encryption key (e.g., the encryption key generated in step S204) to obtain the encrypted additional medical information.

In some embodiments, the encryption method may be a symmetric key encryption method. In this case, the digital abstract of the medical image may be used directly as a symmetric encryption key.

In some embodiments, the encryption method may also be an asymmetric key encryption method. In this case, a private key/public key for encryption/decryption may be derived from the digital digest of the medical image in step S204.

In some embodiments, the encryption may be performed with the private key, and the public key is distributed to respective medical terminals 120 or any other devices or users (e.g., patients) that needs to decrypt the additional medical information.

In some embodiments, the hash value of the medical image is used as the encryption key for the additional medical information. This may guarantee the completeness of the medical image and that the medical image cannot be tampered. If the medical image is tampered, according to the decryption process described below, it can be seen that the decryption key obtained from the tampered medical image will not possibly correspond to the encryption key for encryption, and thus the encrypted additional medical information cannot be decrypted correctly with the decryption key, which indicates that the medical image has been tampered. In addition, encrypting the additional medical information also ensures the security of the additional medical information.

Although in the above embodiment, the additional medical information is first generated, and then the encryption key is determined, the present disclosure is not limited thereto. In other embodiments, the order of the two steps S203 and S204 may be reversed in whole or in part, or performed in parallel. In fact, it is only required to generate the additional medical information and the encryption key before encrypting the additional medical information, and their specific execution orders are not specifically limited.

In step S206, the medical image storage device 110 may transmit the medical image in association with the encrypted additional medical information to the PACS server 130.

It should be noted that step S204 and step S205 are not necessarily performed in the medical image storage device 110 as shown in FIG. 2, but may be performed in whole or in part at other locations, such as the PACS server 130, the medical image generation device 100, or any device. In a case of the PACS server 130, the medical image storage device 110 may transmit to the PACS server 130 the original additional medical information that is not encrypted, rather than the encrypted additional medical information. In a case of the medical image generation device 100, the encryption key for encryption may also be transmitted in step S202, and step S204 need not be performed.

In step S207, the PACS server 130 may store the received medical image and the encrypted additional medical information in association for subsequent use. For example, the PACS server 130 may store all or part of these data in a local or remote database. For another example, in a case where the PACS server 130 is integrated with the medical image storage device 110, step S206 may be omitted, and it directly proceeds to step S207.

Further, although the above description has been illustrated taking the case where the first data are the medical image and the second data are the additional medical information, the present disclosure is not limited thereto. More generally, the first data and the second data may be any data that need the completeness and the non-repudiation to be guaranteed.

Alternatively, in the embodiment as shown in FIG. 1 and FIG. 2, the patient or other person may request the examination report, including, for example, the medical image and the additional medical information, at the medical terminal 120 by, for example, swiping the card, entering the ID number, entering the checklist number, scanning the 2D code, and the like.

For example, the medical terminal 120 may issue the examination report request to the PACS server 130 according to such input in step S210. The examination report request may include an identifier for identifying the patient and/or the corresponding examination (e.g., ID number, checklist number, etc.).

In step S211, the PACS server 130 may search its database according to the received examination report request, or more specifically, according to, for example, the identifier indicating the corresponding medical image and the additional medical information therein, and retrieve the corresponding medical image and the encrypted additional medical information.

In step S212, the PACS server 130 may transmit the medical image (first data) and the encrypted additional medical information (encrypted second data) to the medical terminal 120. After receiving the medical image (first data) and the encrypted additional medical information (encrypted second data), the medical terminal 120 may perform the corresponding decryption process.

For example, in step S213, the medical terminal 120 may generate a decryption key for decrypting the encrypted additional medical information according to the received medical image.

In some embodiments, the encryption method may be a symmetric encryption method, and thus the decryption key may be an encryption key as previously described, such as the digital digest of the medical image.

In some embodiments, the encryption method may be an asymmetric encryption method, and thus the decryption key may be different from the aforementioned encryption key, such as the public key generated from the digital digest of the medical image, and the corresponding encryption key may be a corresponding private key.

In step S214, the encrypted additional medical information may be decrypted with the generated decryption key to obtain the decrypted additional medical information or the original additional medical information. If an unsuccessful decryption occurs or the decrypted data are not data in an expected format and/or with expected content in step S214, it may be determined that the medical image and/or the additional medical information is tampered or erroneous. If a successful decryption occurs or the decrypted data is in the expected format and/or with the expected content, it may be determined that the medical image and the additional medical information are not tampered, and thus are the original data.

Step S213 and step S214 are not necessarily performed in the medical terminal 120 as shown in FIG. 2, but may be performed in whole or in part at other locations, such as the PACS server 130 or the medical image generation device 100. In a case of the PACS server 130, the medical image storage device 110 may transmit to the PACS server 130 the original additional medical information that is not encrypted, rather than the encrypted additional medical information. In a case of the medical image generation device 100, the PACS server 130 may transmit the unencrypted or encrypted additional medical information to medical image storage device 110, rather than the medical terminal 120.

In some embodiments, for a larger medical image, in order to determine its digital digest or hash value, a hash list or a Merkle tree may be used to perform the hashing process. In this case, in an event that there is a problem with the medical image, the problematic data area may be quickly positioned by the data structure provided by the hash list or the Merkle tree. This provides further protection against the data tampering.

In some embodiments, it may be desirable to implement a fast data stream. For example, real-time image data of the patient's injury may be required. To this end, the real-time encryption/decryption may be achieved using the standard DES encryption method.

In some embodiments, in order to avoid increasing the workload of the doctor and/or the patient, the data storage/reading process may be transparent to the operator. That is, at the time of data storage/reading, the digital digest (or the encryption key, the decryption key) of the medical image may be automatically calculated, and the additional information is finely encrypted using the value. Similarly, when the additional information is extracted from the database, the system automatically calculates the hash value of the image, and decrypts the stored information.

Heretofore, a scheme for data storage and reading according to the embodiment of the present disclosure has been described in detail with reference to FIGS. 1 and 2. With this scheme, the additional diagnostic information may be encrypted using the information of the medical image/data, in order to achieve information pairing and prevent tampering or mismatching.

Figure 3:
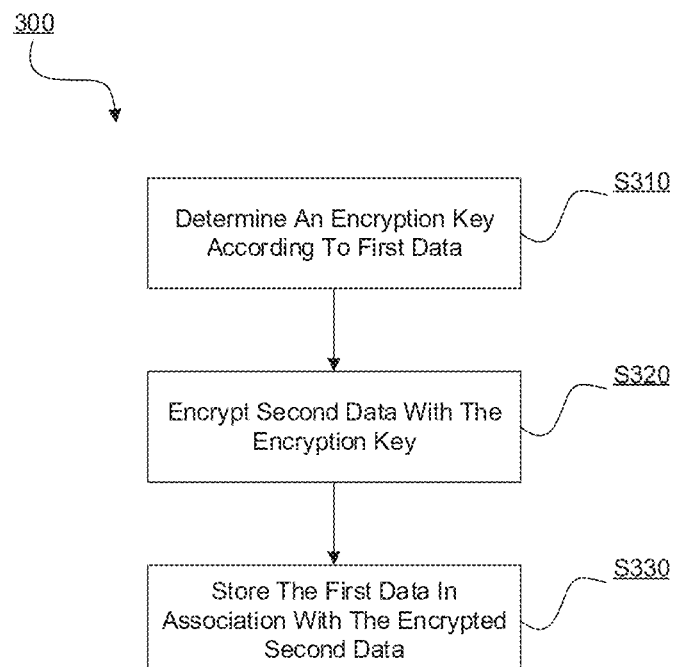
FIG. 3 is a flow chart showing an exemplary method for storing data in accordance with an embodiment of the present disclosure.

FIG. 3 is a flow chart showing a method 300 for storing data in accordance with an embodiment of the present disclosure. As shown in FIG. 3, the method 300 may include steps S310, S320, and S330. According to some embodiments of the present disclosure, some of the steps of the method 300 may be performed separately or in combination, and may be performed in parallel or sequentially, but are not limited to the specific operational order as shown in FIG. 3. In some embodiments, the method 300 may be performed by the medical image storage device 110, the data storage client 115 thereon, the PACS server 130 as shown in FIG. 1, or a data processing device 400 as shown in FIG. 4.

Figure 5:
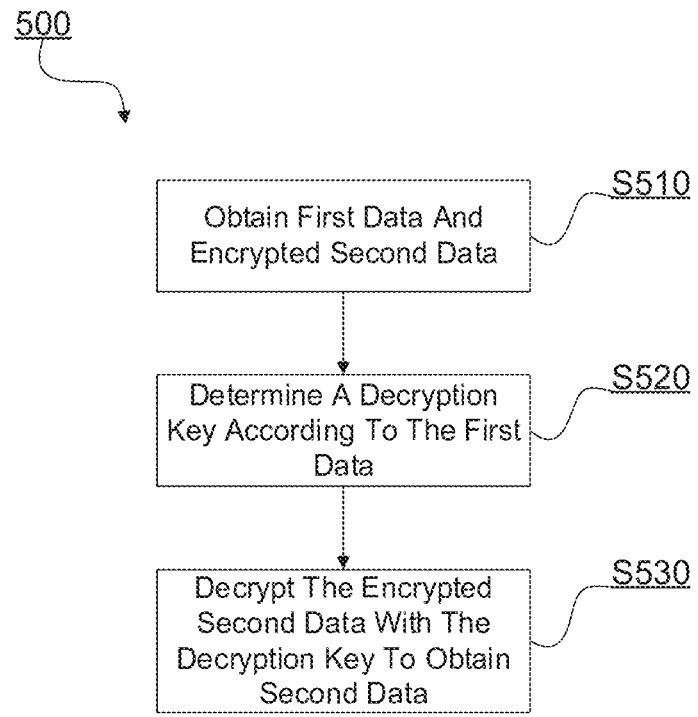
FIG. 5 is a flow chart showing an exemplary method for reading data in accordance with an embodiment of the present disclosure.
Figure 6:
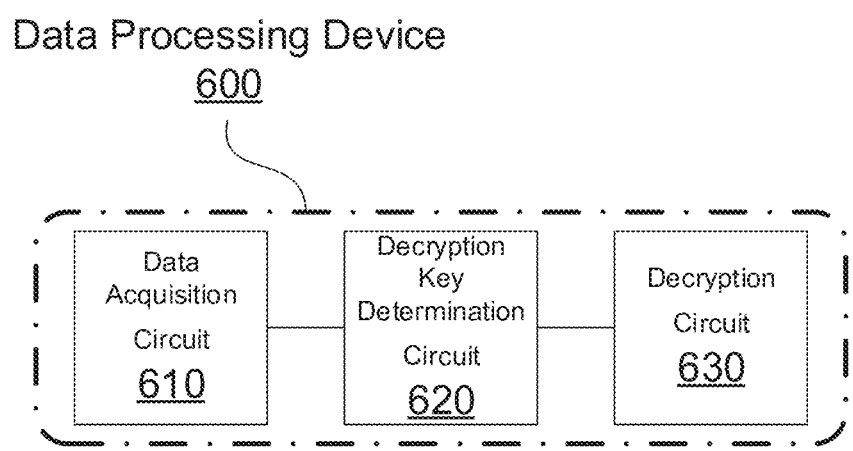
FIG. 6 is a functional block diagram showing an exemplary device for performing the method illustrated in FIG. 5 in accordance with an embodiment of the present disclosure.

FIG. 5 is a flow chart showing a method 500 for reading data in accordance with an embodiment of the present disclosure. As shown in FIG. 5, the method 500 may include steps S510, S520, and S530. According to some embodiments of the present disclosure, some of the steps of the method 500 may be performed separately or in combination, and may be performed in parallel or sequentially, but are not limited to the specific operational sequence as shown in FIG. 5. In some embodiments, the method 500 may be performed by the medical terminal 120, the data reading client 125 thereon, the medical image storage device 110, the data storage client 115 thereon, the PACS server 130 as shown in FIG. 1, or a data processing device 600 as shown in FIG. 6.

Figure 4:
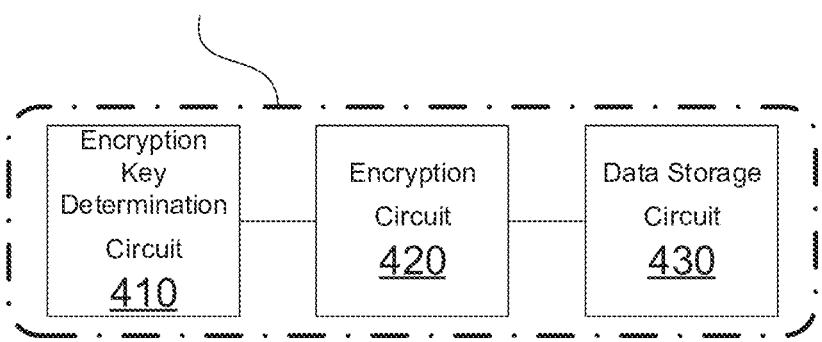
FIG. 4 is a functional block diagram showing an exemplary device for performing the method of FIG. 3 in accordance with an embodiment of the present disclosure.

FIG. 4 is a functional block diagram showing an exemplary device for storing data in accordance with an embodiment of the present disclosure. As shown in FIG. 4, the data processing device 400 may include an encryption key determination circuit 410, an encryption circuit 420, and a data storage circuit 430.

The encryption key determination circuit 410 may be configured to determine an encryption key based on the first data. For example, the encryption key determination circuit 410 may be a processor of the device 400, and the encryption key determination circuit 410 may be coupled to the communication device and/or the storage device of the device 400 for determining the encryption key for encrypting the second data according to the received or retrieved first data. The encryption key may be, for example, the digital digest of the first data.

The encryption circuit 420 may be configured to encrypt the second data using the encryption key. The encryption circuit 420 may also be a processor of the device 400, which may be coupled to the communication device and/or the storage device of the device 400, and use the encryption key determined by the encryption key determination circuit 410 to encrypt the received or retrieved second data. The encryption method may be, for example, a symmetric encryption algorithm or an asymmetric encryption algorithm.

The data storage circuit 430 may be configured to store the first data in association with the encrypted second data. The data storage circuit 430 may be coupled to the processor of the device 400 and/or the storage device of the device 400 by the communication device of the device 400, or integrated in the storage device of the device 400, so as to store the first data and the encrypted second data in association locally, or transmit them to a remote data storage device for remote storage.

For example, the device 400 may include one or more processors. The encryption key determination circuit 410 and the encryption circuit 420 may be integrated in the same processor of the device, or the encryption key determination circuit 410 and the encryption circuit 420 may be located at different processors.

For example, the processor of the device 400 may be a central processing circuit (CPU), a digital signal processor (DSP), a microprocessor, a microcontroller, an application specific integrated circuit (ASIC), a programmable logic array (FPGA), or any other circuits capable of logic operations.

For example, the communication device may be a wireless transceiver, a wireless network card, an Ethernet card, an xDSL modem, Bluetooth, or the like.

For example, the storage device may be RAM, ROM, SD, MicroSD, CF, SSD, HD, Tape, or the like.

The data processing device 400 may also include other circuitry not shown in FIG. 4, such as a bus, a power supply, an antenna, a communication device, a storage device. However, they do not affect the understanding of the principles of the present application, and thus their detailed descriptions are omitted herein.

FIG. 6 is a functional block diagram showing an exemplary data processing device 600 for reading data in accordance with an embodiment of the present disclosure. As shown in FIG. 6, the data processing device 600 may include a data acquisition circuit 610, a decryption key determination circuit 620, and a decryption circuit 630.

The data acquisition circuit 610 may be configured to acquire first data and encrypted second data. The data acquisition circuit 610 may be coupled to the processor of the device 600 and/or the storage device of the device 600 by the communication device of the device 600, or integrated in the storage device of the device 600, so as to receive the first data and the encrypted second data from the remote device, or retrieve the first data and the encrypted second data from the local database.

The decryption key determination circuit 620 may be configured to determine a decryption key based on the first data. The decryption key determination circuit 620 may be a processor of the data processing device 600 that may be coupled to the communication device and/or storage device of the data processing device 600. The decryption key determination circuit 620 may determine, according to the first data received or retrieved by the data acquisition circuit 610, the decryption key for decrypting the encrypted second data. The decryption key may be, for example, the digital digest of the first data or other keys derived from the digital digest.

The decryption circuit 630 may be configured to decrypt the encrypted second data with the decryption key to obtain the second data. The decryption circuit 630 may be a processor of the data processing device 600 that may be coupled to the communication device and/or storage device of the data processing device 600. The decryption circuit 630 may decrypt the encrypted second data with the decryption key determined by the decryption key determination circuit 620 to obtain the decrypted second data or the original second data. If the decryption is successful, both the first data and the second data are complete and are not tampered. If the decryption fails, for example, the second data cannot be decrypted, or the decrypted second data does not have the expected format and/or content, the first data and/or the second data are tampered or corrupted.

For example, the device 600 may include one or more processors. The decryption key determination circuit 620 and the decryption circuit 630 may be integrated in the same processor of the device, or the decryption key determination circuit 620 and the decryption circuit 630 may be located in different processors.

For example, the processor of device 600 may be a central processing circuit (CPU), a digital signal processor (DSP), a microprocessor, a microcontroller, an application specific integrated circuit (ASIC), a programmable logic array (FPGA), or any other circuits capable of logic operations.

For example, the communication device may be a wireless transceiver, a wireless network card, an Ethernet card, an xDSL modem, Bluetooth, or the like.

For example, the storage device may be RAM, ROM, SD, MicroSD, OF, SSD, HD, Tape, or the like.

In addition, the data processing device 600 may further include other circuits not shown in FIG. 6, such as a bus, a memory, a power supply, an antenna, a communication portion, and a storage portion. However, they do not affect the understanding of the principles of the present application, and thus their detailed descriptions are omitted herein.

Hereinafter, the method 300 performed at the data processing device 400 for processing data and the data processing device 400 in accordance with an embodiment of the present disclosure will be described in detail with reference to FIGS. 3 and 4.

In step S310, the encryption key may be determined by the encryption key determination circuit 410 of the data processing device 400 according to the first data.

In step S320, the second data may be encrypted by the encryption circuit 420 of the data processing device 400 with the encryption key.

In step S330, the first data may be stored in association with the encrypted second data by the data storage circuit 430 of the data processing device 400.

In some embodiments, the encryption key may be the digital digest of the first data. Step S310 includes: determining the digital digest of the first data as the encryption key. In this way, the encryption key is guaranteed to be unforgeable while the completeness of the first data is guaranteed. In some embodiments, the encryption key may be a symmetric encryption key. Step S320 includes: generating a symmetric encryption key as the encryption key using a symmetric encryption algorithm. In this way, the key may be used for both encryption and decryption, saving the key generation time. In some embodiments, the first data may be a medical image, and the second data may be additional diagnostic information associated with the medical image. In this case, the technical solution according to the present disclosure may be used in the field of medical image management, and thus doctor-patient disputes may be avoided. In some embodiments, the digital digest may be determined by a hash list or a Merkle tree. In this way, the problematic data area may be positioned when there is a problem with the first data. In some embodiments, the encryption method may be a Data Encryption Standard (DES) encryption algorithm. Step S330 includes: encrypting the second data with a data encryption standard "DES" encryption algorithm. In this way, the real-time encryption may be achieved.

Hereinafter, the method 500 performed at the data processing device 600 for processing data and the data processing device 600 in accordance with an embodiment of the present disclosure will be described in detail with reference to FIGS. 5 and 6.

In step S510, the first data and the encrypted second data may be acquired by the data acquisition circuit 610 of the data processing device 600.

In step S520, the decryption key may be determined according to the first data by the decryption key determination circuit 620 of the data processing device 600.

In step S530, the encrypted second data may be decrypted by the decryption circuit 630 of the data processing device 600 with the decryption key to obtain the second data.

In some embodiments, the decryption key may be the digital digest of the first data. Step S510 includes: determining the digital digest of the first data as the decryption key. In this way, the decryption key is guaranteed to be unforgeable while the completeness of the first data is guaranteed. In some embodiments, the decryption key may be a symmetric decryption key. Step S520 includes: generating a symmetric decryption key as the decryption key using a symmetric encryption algorithm. In this way, the key may be used for both encryption and decryption, saving the key generation time. In some embodiments, the first data may be a medical image, and the second data may be additional diagnostic information associated with the medical image. In this case, the technical solution according to the present disclosure may be used in the field of medical image management, and thus doctor-patient disputes may be avoided. In some embodiments, the digital digest may be determined by a hash list or a Merkle tree. In this way, the problematic data area may be positioned when there is a problem with the first data. In some embodiments, the decryption method may be a Data Encryption Standard (DES) decryption algorithm. Step S530 includes: decrypting the encrypted second data with a data encryption standard "DES" decryption algorithm. In this way, the real-time decryption may be achieved.

Figure 7:
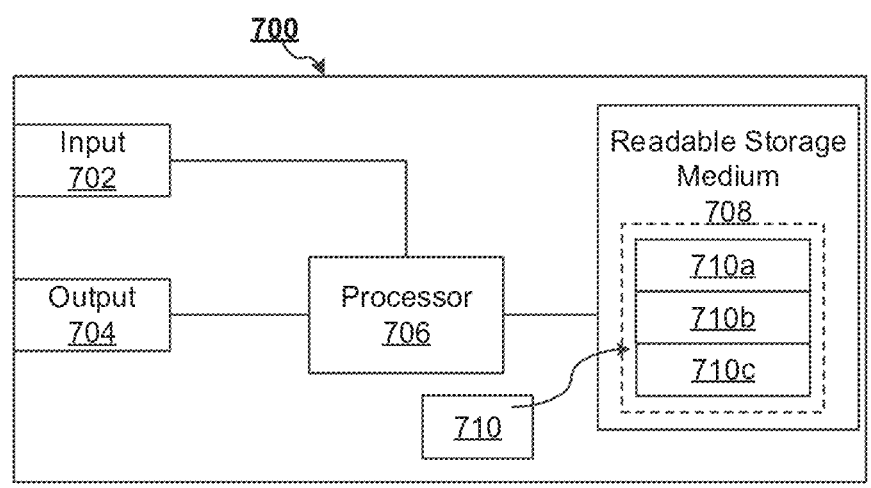
FIG. 7 is a hardware layout diagram showing an exemplary device for storing and/or reading data in accordance with an embodiment of the present disclosure.

FIG. 7 is a block diagram showing an exemplary hardware arrangement 700 of the data processing device 400 of FIG. 4, or the data processing device 600 of FIG. 6, in accordance with an embodiment of the present disclosure. The hardware arrangement 700 may include one or more processors 706, e.g., a central processing circuit (CPU), a digital signal processor (DSP), a microprocessor, a microcontroller, an application specific integrated circuit (ASIC), a programmable logic array (FPGA), etc. The arrangement 700 may also include an input circuit 702 for receiving signals from other entities, and an output circuit 704 for providing signals to other entities. The input circuit 702 and the output circuit 704 may be arranged as a single entity or as separate entities.

Moreover, the arrangement 700 may include at least one readable storage medium 708 in the form of a non-volatile or volatile memory, such as an electrically erasable programmable read only memory (EEPROM), flash memory, and/or a hard drive. The readable storage medium 708 may include a computer program 710 that includes code/computer readable instructions that, when executed by the processor 706 in the arrangement 700, cause the hardware arrangement 700 and/or the data processing device 400 or the data processing device 600 including the hardware arrangement 700 to perform, for example, the processes described above in connection with FIG. 2, FIG. 3, or FIG. 5, and any variations thereof.

Computer program 710 may be configured as computer program codes having, for example, an architecture of computer program module 710A-710C. Accordingly, in an exemplary embodiment in which for example, the hardware arrangement 700 is used in the device 400, the codes in the computer program of the arrangement 700 include a module 710A for determining an encryption key according to first data. The codes in the computer program further include a module 710B for encrypting second data with the encryption key. The codes in the computer program further include a module 710C for storing the first data in association with the encrypted second data.

Moreover, in an exemplary embodiment in which, for example, the hardware arrangement 700 is used in the device 600, the codes in the computer program of the arrangement 700 include a module 710A for acquiring first data and encrypted second data. The codes in the computer program further include a module 710B for determining a decryption key according to the first data. The codes in the computer program further include a module 710C for decrypting the encrypted second data with the decryption key to obtain the second data.

The computer program module may substantially perform various actions in the flow shown in FIG. 2, FIG. 3, or FIG. 5 to simulate the device 400 or 600. In other words, when different computer program modules are executed in the processor 706, they may correspond to the different circuits or modules described above in the data processing device 400 or the data processing device 600.

Although the code means in the embodiment disclosed above in connection with FIG. 7 is implemented as a computer program module that, when executed in processor 706, causes the hardware arrangement 700 to perform the actions described above in connection with FIG. 2, FIG. 3, or FIG. 5, at least one of the code means may be implemented at least in part as a hardware circuit in an alternative embodiment.

The processor may include a general purpose microprocessor, an instruction set processor, and/or a related chipset and/or a special purpose microprocessor. The processor may also include an onboard memory for caching purposes. The computer program may be carried by a computer program product connected to the processor. The computer program product may comprise a computer readable medium having stored thereon a computer program. For example, the computer program product may be flash memory, random access memory (RAM), read only memory (ROM), EEPROM, and the computer program modules described above may be distributed to different computer program products in the form of memory within the UE in alternative embodiments.

The present disclosure has been described so far in connection with the embodiments. It will be appreciated that various other changes, substitutions and additions may be made by those skilled in the art without departing from the spirit and scope of the disclosure. Therefore, the scope of the present disclosure is not limited to the specific embodiments described above, but is defined by the appended claims.

In addition, the functions described herein as being implemented by pure hardware, software, and/or firmware may also be implemented by dedicated hardware, a combination of general-purpose hardware and software, and the like. For example, functions described as being implemented by dedicated hardware (e.g., Field Programmable Gate Array (FPGA), Application Specific Integrated Circuit (ASIC), etc.) may be performed by general purpose hardware (e.g., central processing unit (CPU), digital signal processing (DSP) is implemented in a way that is combined with software and vice versa.

I claim:

1. A data processing method, comprising:
    determining an encryption key according to first data;
    encrypting second data with the encryption key;
    storing the first data in association with the encrypted second data,
    acquiring the first data and the encrypted second data;
    determining a decryption key according to the first data; and
    decrypting the encrypted second data with the decryption key to obtain the second data,
    wherein the first data comprises a medical image, and the second data comprises additional information associated with the medical image,
    wherein the additional information is a diagnostic report corresponding to the medical image,
    wherein the determining the encryption key according to the first data comprises determining a digital digest of the first data as the encryption key, and
    wherein the determining the decryption key according to the first data comprises determining a digital digest of the first data as the decryption key.

2. The data processing method of claim 1, wherein the determining the encryption key according to the first data comprises: generating a symmetric encryption key as the encryption key using a symmetric encryption algorithm.

3. The data processing method of claim 2, wherein the encrypting the second data with the encryption key comprises: encrypting the second data using a data encryption standard "DES" encryption algorithm.

4. The data processing method of claim 1, wherein the digital digest is determined by a hash list or a Merkle tree.

5. The data processing method of claim 1, wherein the determining the decryption key according to the first data comprises: generating a symmetric decryption key as the decryption key using a symmetric encryption algorithm.

6. The data processing method of claim 5, wherein the decrypting the encrypted second data with the decryption key comprises: decrypting the encrypted second data using a data encryption standard "DES" decryption algorithm.

7. A data processing device, comprising:
    a processor; and
    a memory storing instructions that, when executed by the processor, cause the processor to perform the method of claim 1.

8. The data processing device of claim 7, wherein the instructions, when executed by the processor, further cause the processor to:
    determine a digital digest of the first data as the decryption key; or
    generate a symmetric decryption key as the decryption key using a symmetric encryption algorithm.

9. A computer readable storage medium storing instructions which, when executed by a processor, cause the processor to perform one or more steps of the method of claim 1.

10. A data processing device, comprising:
    a processor; and
    a memory storing instructions that, when executed by the processor, cause the processor to:
    determine an encryption key according to first data;
    encrypt second data with the encryption key;
    store the first data in association with the encrypted second data,
    acquire the first data and the encrypted second data;
    determine a decryption key according to the first data; and
    decrypt the encrypted second data with the decryption key to obtain the second data,
    wherein the first data comprises a medical image, and the second data comprises additional information associated with the medical image,
    wherein the additional information is a diagnostic report corresponding to the medical image,
    wherein the determining the encryption key according to the first data comprises determining a digital digest of the first data as the encryption key, and
    wherein the determining the decryption key according to the first data comprises determining a digital digest of the first data as the decryption key.

11. The data processing device of claim 10, wherein the instructions, when executed by the processor, further cause the processor to:
    determine a digital digest of the first data as the encryption key; or
    generate a symmetric encryption key as the encryption key using a symmetric encryption algorithm.

12. The data processing device of claim 10, wherein the instructions, when executed by the processor, further cause the processor to:
    encrypt the second data using a data encryption standard "DES" encryption algorithm.

* * * * *